United States Patent [19]
Callne

[11] Patent Number: 5,645,425
[45] Date of Patent: Jul. 8, 1997

[54] DISPOSABLE DENTAL ARTICULATOR

[75] Inventor: Lars E. Callne, San Jose, Calif.

[73] Assignee: Nu-Logic Dental Mfg., Inc., Lyons, Ill.

[21] Appl. No.: 667,065

[22] Filed: Jun. 20, 1996

[51] Int. Cl.⁶ .................................................. A61C 11/00
[52] U.S. Cl. .................... 433/54; 433/57; 433/60
[58] Field of Search ................. 433/54, 57, 60, 433/64

[56] References Cited

U.S. PATENT DOCUMENTS

| | | | |
|---|---|---|---|
| 4,252,523 | 2/1981 | Gayso | 433/60 |
| 4,382,787 | 5/1983 | Huffman . | |
| 4,496,320 | 1/1985 | Hwang et al. | 433/60 |
| 5,076,786 | 12/1991 | Callne . | |
| 5,221,203 | 6/1993 | Callne . | |
| 5,360,337 | 11/1994 | Westdyk . | |
| 5,482,460 | 1/1996 | Farnor, Jr. et al. . | |

*Primary Examiner*—Nicholas D. Lucchesi
*Attorney, Agent, or Firm*—Thomas E. Schatzel; Law Offices of Thomas E. Schatzel a Prof. Corporation

[57] ABSTRACT

A dental model and articulator system comprises upper and lower dental casts that each receive a corresponding anchor in their respective vertical posterior faces. A generally rectangular articulator main body has a transverse horizontal hinge attachment on its top that connects to an upper arm and the anchor on the upper dental cast. A vertical pivot is provided in the bottom end of the articulator main body that connects to the anchor on the lower dental cast. The upper and lower anchors attach to their respective articulator parts with a stem-in-sleeve arrangement that allows independent lateral tilting of both the upper and lower dental casts for occlusal and masticatory registration and fixing with glue. The vertical pivot also attaches to the articulator main body with a stem-in-sleeve arrangement that allows further degrees of freedom for the occlusal and masticatory registration between the upper and lower dental casts and for fixing the registration with glue. The anchors are secured to their respective dental casts by either gluing the anchor to a slot in the dental cast or by casting the anchor in the dental cast during the molding process.

8 Claims, 3 Drawing Sheets

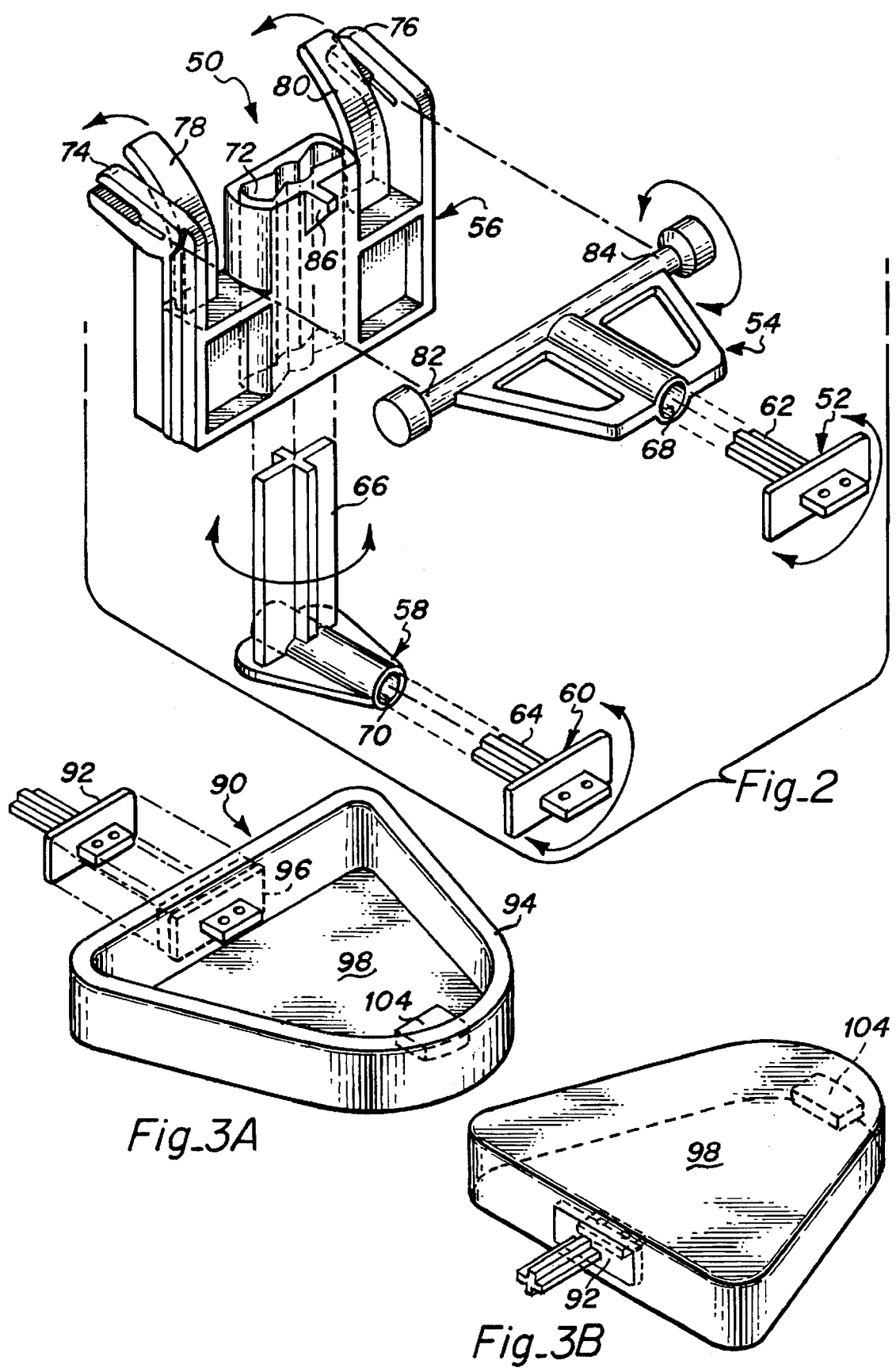

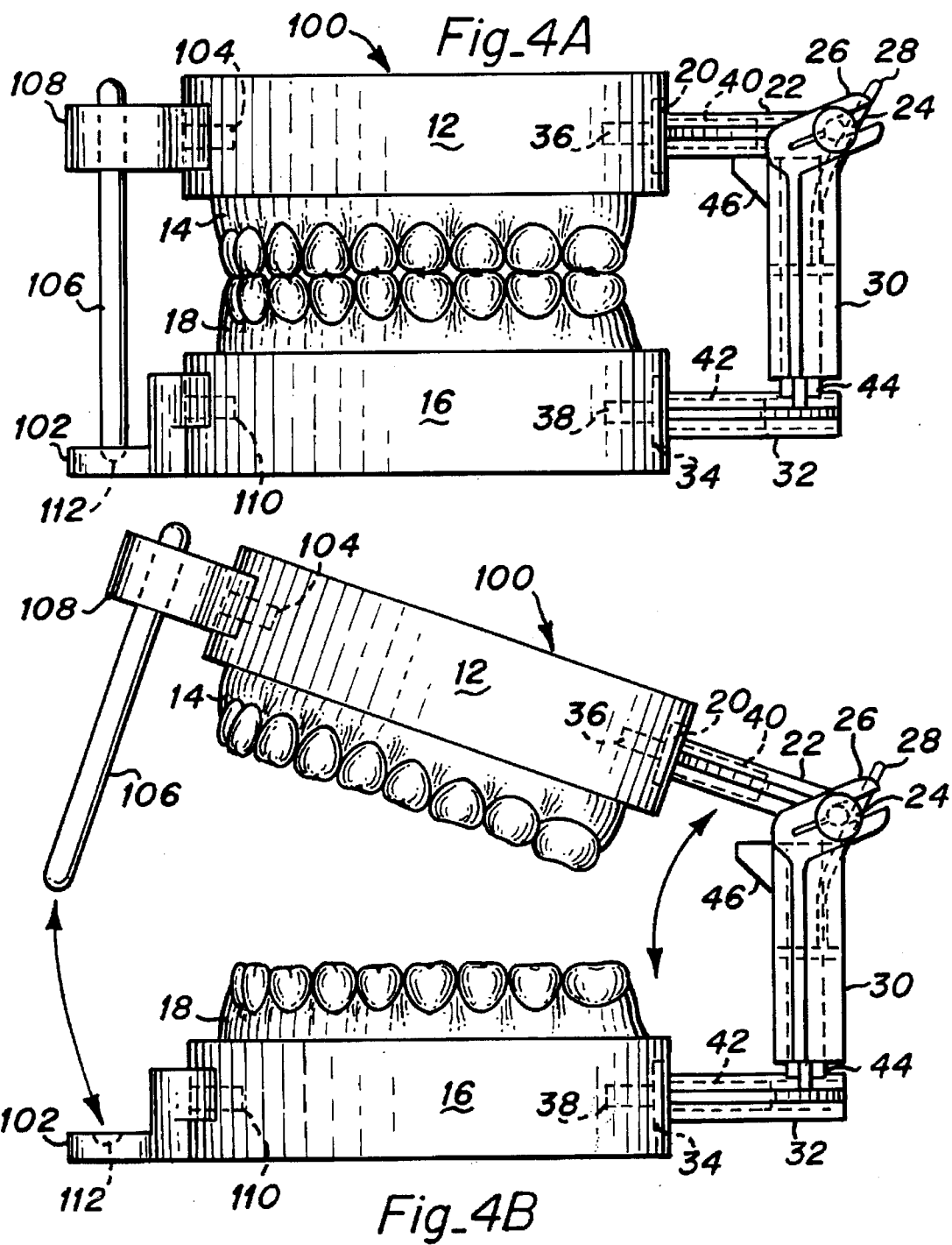

DISPOSABLE DENTAL ARTICULATOR

BACKGROUND OF THE INVENTION

1. Field of the Invention

The invention relates generally to articulators and correlators for registering upper and lower dental casts and more specifically to disposable articulators that can be permanently attached to the dental casts and inexpensive enough to accompany them from the dental lab to the client doctor and then to be disposed after use.

2. Description of the Prior Art

The comprehensive treatment of dental patients includes the casting and modeling of both the patient's teeth and the full range of occlusal and masticatory registration characteristics. Good models allow the doctor to work out the procedures and prosthetics that will ultimately be necessary to treat the condition with a minimum of personal visits by the patient to the doctor's office.

Ronald E. Huffman describes an inexpensive throw away articulator for dental models in U.S. Pat. No. 4,382,787, issued May 10, 1983, which patent is incorporated herein by reference. Upper and lower dental model casts are prepared with a flat face and slot at the rear of each cast. A hinged articulator is attached on opposite ends to each of the casts by anchors that are glued into each of the slots. The articulator hinge is connected to each anchor by a snap in ball joint that allows the proper spatial relationship between the upper and lower casts to be adjusted. Such ball joints may be filled with glue to fix the adjustment once made. In practice, such articulators are not as stiff and rigid as could be desired, thus the registration changes with even modest flexing and twisting.

A dental model articulator that appears better able to resist flexing and twisting is described by Farnor, Jr., et al., in U.S. Pat. No. 5,482,460, issued Jan. 9, 1996, and incorporated herein by reference. A wide hinge has top and bottom vertical channels on its front face that receive mating ears from the top and bottom anchors attached to the rear slots in the top and bottom dental model casts. A technician holds the casts in occlusion and presses the anchor ears into their respective hinge channels filled with fast setting glue. After a few seconds, the articulator becomes fixed with the proper occlusion and the hinge can be opened to manipulate the casts.

Alan M. Westdyk describes in U.S. Pat. No. 5,360,337, issued Nov. 1, 1994, a dental articulator in which the cast anchors are placed in the rear wall of the tray molds for the dental casts and are partially embedded. After curing and setting, the dental casts and anchors are removed from the tray molds and assembled to the articulator.

The prior art has not fully satisfied the need to have high performance articulator systems that maintain their occlusal and masticatory registration with ordinary handling and that can offer the advantage of costs that are low enough to make such articulators disposable after use.

SUMMARY OF THE PRESENT INVENTION

It is therefore an object of the present invention to provide a dental model and articulator system that maintains its occlusal and masticatory registration with ordinary handling.

It is another object of the present invention to provide a dental articulator that is inexpensive and that allows for disposability after use.

Briefly, a dental model and articulator system of the present invention comprises upper and lower dental casts that each receive a corresponding anchor in their respective vertical posterior faces. A generally rectangular articulator main body has a transverse horizontal hinge attachment on its top that connects to an upper arm and the anchor on the upper dental cast. A vertical pivot is provided in the bottom end of the articulator main body that connects to the anchor on the lower dental cast. The upper and lower anchors attach to their respective articulator parts with a stem-in-sleeve arrangement that allows independent lateral tilting of both the upper and lower dental casts for occlusal and masticatory registration and fixing with glue. The vertical pivot also attaches to the articulator main body with a stem-in-sleeve arrangement that allows further degrees of freedom for the occlusal and masticatory registration between the upper and lower dental casts and for fixing the registration with glue. The anchors are secured to their respective dental casts by either gluing the anchor to a slot in the dental cast or by casting the anchor in the dental cast during the molding process.

An advantage of the present invention is that a dental model and articulator system is provided that maintains its occlusal and masticatory registration with ordinary handling.

Another advantage of the present invention is that a dental articulator is provided that is inexpensive and that allows for disposability after use.

These and many other objects and advantages of the present invention will no doubt become obvious to those of ordinary skill in the art after having read the following detailed description of the preferred embodiments which are illustrated in the various drawing figures.

IN THE DRAWINGS

FIG. 2 is an exploded assembly view of a dental cast articulator of the present invention;

FIGS. 3A and 3B are perspective views of a system for partially embedding articulator anchors into dental casts during the molding process; and FIGS. 4A and 4B are side views of a second dental model and articulator system embodiment of the present invention in the closed and open positions and including an incisor pin arrangement to provide stability and additional closing limits.

DETAILED DESCRIPTION OF THE PREFERRED EMBODIMENTS

Figure 1A:
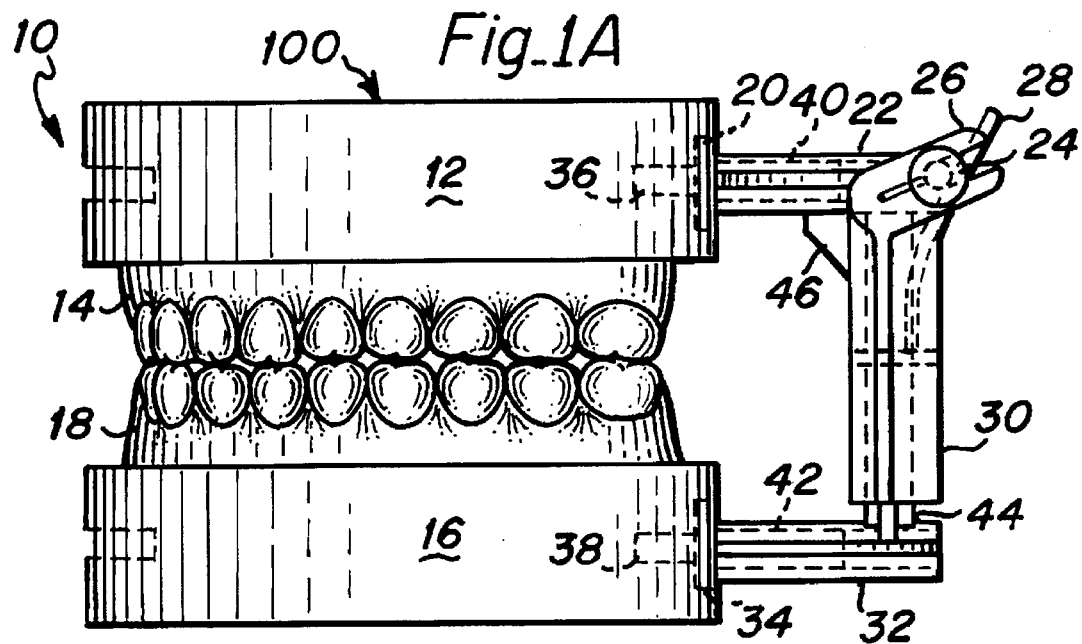
FIGS. 1A and 1B are side views of a first dental model and articulator system embodiment of the present invention in the closed and open positions.
Figure 1B:
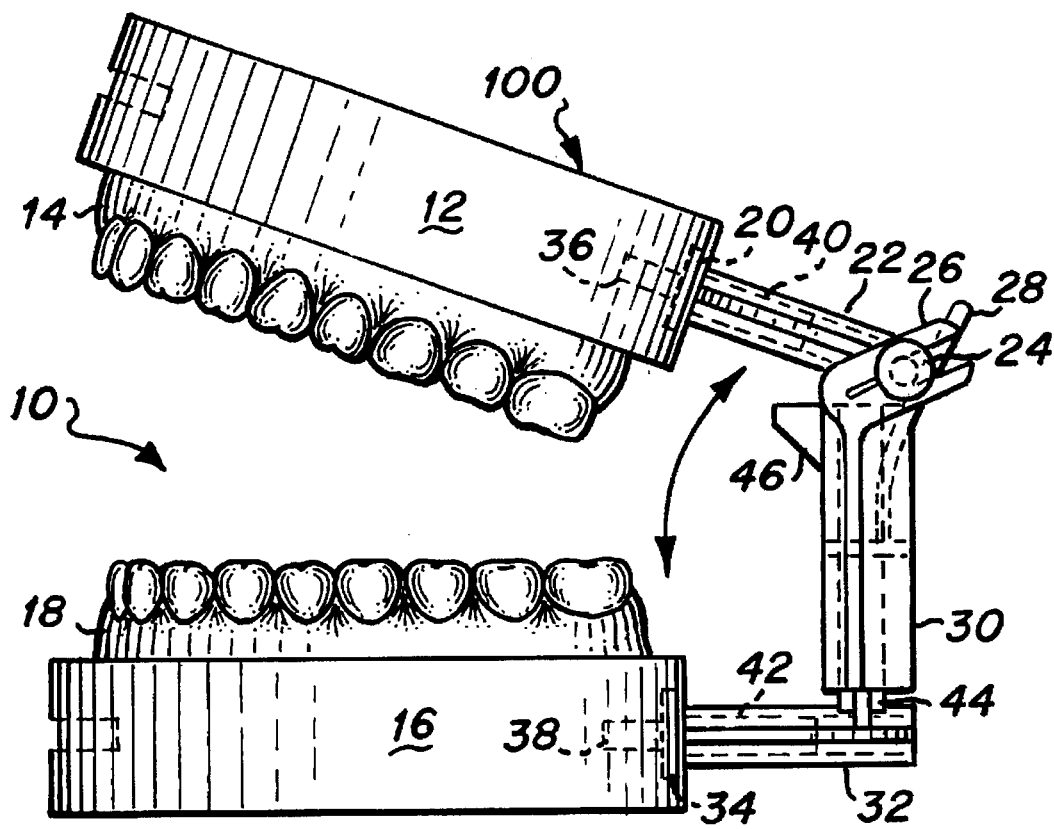

FIGS. 1A and 1B illustrate a dental model and articulator system embodiment of the present invention, referred to herein by the general reference numeral 10. The system 10 comprises an upper (maxilla) base 12 with an upper teeth cast 14 and a lower (mandible) base 16 with a lower teeth cast 18 connected together by an articulator that includes an upper anchor 20 connected to an upper articulator arm 22, a hinge 24 held in a slot arm 26 by a flat spring 28, an articulator stand 30, and a lower pivot 32 connected to a lower anchor 34. For example, the upper and lower bases 12 and 16 may comprise a tray model system for quadrants or full arches, such as is sold commercially by Nu.Logic Dental Manufacturing, Inc., (Lyons, IL) under the E-Z TRAY trademark. The upper and lower anchors 20 and 34 are secured to the upper and lower bases 12 and 16 by gluing a forward tab 36 and 38 on the anchor into a horizontal slot in the rear vertical face of the bases. Alternatively, the anchors can be secured by casting the bases 12 and 16 with the anchor mounted to the base mold such that the forward tab embeds into the material after curing.

An x-cross-section anchor stem 40 attached to the upper anchor 20 slips into a mating cylindrical sleeve in the upper articulator arm 22. The relative fore and aft position and left and right tilt of the upper base 12 may be adjusted and then fixed by filling the x-cross-section stem 40 with glue in the sleeve.

Similarly, another x-cross-section anchor stem 42 attached to the lower anchor 34 slips into a mating cylindrical sleeve in the lower articulator pivot 32. The relative fore and aft position and left and right tilt of the lower base 16 may be adjusted and then fixed by filling the x-cross-section stem 42 with glue in the sleeve in the lower articulator pivot 32.

An x-cross-section pivot stem 44 attached to 10 the pivot 32 slips into a mating cylindrical sleeve in the articulator stand 30. The height and the relative lateral pivot of the upper base 12 to the lower base 16 may be adjusted and then fixed by filling the x-cross-section stem 44 with glue in the sleeve of the articulator stand 30.

The upper articulator arm 22 snaps into place in the left and right slot arms 26 formed at the top of the articulator stand 30. Left and right flat springs 28 retain the hinge 24 in the left and right slot arms 26 and allow rotation of the upper and lower bases 12 and 16 on the axis of the hinge 24. The closing of the upper and lower bases 12 and 16 is limited by a stop 46 molded into and protruding from the front surface of the articulator stand 30.

A particular embodiment of the present invention is shown in FIG. 2 as an articulator 50, and is similar in purpose and function to that shown in FIG. 1. The material used for the various parts of the articulator 50 may be of ABS plastic. An upper anchor 52 fits into an upper arm 54. A main body 56 makes a hinge attachment with the upper arm 54 at its top end and a pivotable attachment with a pivot 58 at its lower end. A lower anchor 60 plugs into the pivot 58.

The anchors 52 and 60 and pivot 58 each have an x-cross-section stem 62, 64, and 66, respectively, that each allow for rotation within their mating sleeves 68, 70 and 72 when dry, e.g., ±40° for occlusal and masticatory registration of upper and lower dental casts by a technician. The grooves on the sides of each of the stems allow glue to be introduced into the sleeve to permit permanent fixing once the desired dental registration has been adjusted into the model.

A pair of left and right slotted ears 74 and 76, and retaining springs 78 and 80, receive and hold corresponding pair of coaxial hinge axles 82 and 84. Such provide for a horizontal hinge action that is transverse and posterior to the registered dental casts held by the anchors 52 and 60. A stop 86 prevents the upper arm 54 from rotating too far downward, and prevents too hard a closure of the upper and lower dental casts.

FIGS. 3A and 3B illustrate a system for partially embedding an anchor 92, similar to the upper and lower dental cast anchors 20, 34, 52, and 60, into a dental cast during a molding process. The anchor 92 is inserted into a soft flexible tray mold 94 with a window 96. A cast material is poured into the mold tray 94 while the anchor 92 is in place in the window 96 and is allowed to set. A cast 98 with the partially embedded anchor 92 is withdrawn from the mold 94 after curing.

FIGS. 4A and 4B show a dental model and articulator system embodiment of the present invention, referred to herein by the general reference numeral 100. The dental model and articulator system 100 provides increased stability, e.g., for bridge construction by a technician, where a significant number of teeth are missing from the upper and lower casts 12 and 16 and could allow unusual twisting and misregistration. A stop 102 is mounted in a slot 110 in the lower dental cast 16. The slot 110 runs horizontally and is positioned in the front vertical face of the incisor area. A rib may be provided in the mold tray 98 to cast in the slot 110. A pin 106 engages the Stop 102 and fits in a table 108. A slot 104 is horizontally oriented and positioned in the front vertical face of the incisor area of the upper dental cast 12. The table 108 is glued to the slot 104 and a spot of glue may be used to fix the vertical position of the pin 106 in the table 108. The pin 106 preferably has a round end that engages a well 112 in the stop 102.

Although the present invention has been described in terms of the presently preferred embodiments, it is to be understood that the disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. A dental model and articulator system (10), comprising:
   a pair of upper and lower dental casts (12, 16) each with a corresponding anchor (20, 34) in their respective vertical posterior faces;

an articulator main body (30) with a transverse horizontal hinge attachment (24, 26, 28) on its top that detachably connects to an upper arm (22) and the upper dental cast anchor (20);

a vertical pivot (32) provided in the bottom end of the articulator main body (30) that connects to the lower dental cast anchor (34);

an upper dental cast anchor stem-in-sleeve arrangement (40) that attaches the upper dental cast anchor (20) to said upper arm (22) and that provides for independent lateral tilting of the upper dental cast (12) for occlusal and masticatory registration and for fixing at least one aspect of said registration;

a lower dental cast anchor stem-in-sleeve arrangement (42) that attaches the lower dental cast anchor (34) to the vertical pivot (32) and that provides for independent lateral tilting of the lower dental cast for occlusal and masticatory registration and for fixing at least one aspect of said registration; and a pivot stem-in-sleeve arrangement (44) that attaches the vertical pivot (32) to the articulator main body (30) and that provides for occlusal and masticatory registration of the upper and lower dental casts (12, 16) and for fixing at least one aspect of said registration.

2. The system of claim 1, wherein:
   the upper and lower dental cast anchors (20, 34) are secured to their respective dental casts (12, 16) by gluing the anchor to a slot in the dental cast.

3. The system of claim 1, wherein:
   the upper and lower dental cast anchors (20, 34) are partially embedded in their respective dental casts (12, 16) by casting the anchor into the dental cast during a molding process.

4. The system of claim 1, further comprising:

a stop (46) positioned between the articulator main body (30) and said upper arm (22) and providing for a limit of the closing range permitted for the upper and lower dental casts (12, 16).

5. The system of claim 1, further comprising:

an incisor limiting means (102–112) disposed between the front ends of the upper and lower dental casts (12, 16), opposite of the respective mountings of the upper and lower dental cast anchors (20, 34), and providing for a limit of the closing range permitted for the upper and lower dental casts (12, 16).

6. The system of claim 5, wherein:

the incisor limiting means comprises a stop (102) mounted to a slot (110) in the vertical face of an incisor area of the lower dental cast (12), and a pin (106) held by a table (108) mounted to a slot (104) in the vertical face of an incisor area of the upper dental cast (16).

7. A dental cast articulator (50), comprising:

a pair of upper and lower anchors (52, 60) for attachment to corresponding upper and lower dental casts in their respective vertical posterior faces;

an articulator main body (56) with a transverse horizontal hinge attachment (74, 76, 78, 80, 82, 84) on its top that detachably connects to an upper arm (54) and the upper dental cast anchor (52);

a vertical pivot (58) provided in the bottom end of the articulator main body (56) that connects to the lower dental cast anchor (60);

an upper dental cast anchor stem-in-sleeve arrangement (62, 68) that attaches the upper dental cast anchor (52) to said upper arm (54) and that provides for independent lateral tilting of an upper dental cast for occlusal and masticatory registration and for fixing at least one aspect of said registration;

a lower dental cast anchor stem-in-sleeve arrangement (64, 70) that attaches the lower dental cast anchor (60) to the vertical pivot (58) and that provides for independent lateral tilting of an lower dental cast for occlusal and masticatory registration and for fixing at least one aspect of said registration; and a pivot stem-in-sleeve arrangement (66, 72) that attaches the vertical pivot (58) to the articulator main body (56) and that provides for occlusal and masticatory registration of said upper and lower dental casts and for fixing at least one aspect of said registration.

8. The articulator (50) of claim 7, further comprising:

a stop (86) that provides for a limit to the range of rotation of said transverse horizontal hinge attachment (74, 76, 78, 80, 82, 84) and disposed between the upper arm (54) and the articulator main body (56).

* * * * *